878
United States Patent [19]
Pars et al.

[11] 3,994,922
[45] Nov. 30, 1976

[54] BENZOPYRANS AND INTERMEDIATES FOR THE PREPARATION OF PYRROLO BENZOPYRANS

[75] Inventors: Harry G. Pars, Lexington; Raj K. Razdan, Belmont, both of Mass.

[73] Assignee: Arthur D. Little, Inc., Cambridge, Mass.

[22] Filed: Nov. 29, 1974

[21] Appl. No.: 528,011

Related U.S. Application Data

[60] Division of Ser. No. 332,404, Feb. 14, 1973, Pat. No. 3,888,946, which is a continuation-in-part of Ser. No. 144,244, March 17, 1971, abandoned, which is a continuation-in-part of Ser. No. 842,690, July 17, 1969, abandoned.

[52] U.S. Cl. .............................................. 260/326.29
[51] Int. Cl.² ......................................... C07D 491/04
[58] Field of Search ................................. 260/326.29

[56] References Cited
UNITED STATES PATENTS

3,862,143  1/1975  Klutchko ...................... 260/326.29

OTHER PUBLICATIONS

Adams et al., J. Amer. Chem. Soc. 71, 1624 (1949).

Pars et al., J. Med. Chem. 19, 445–454 (1976).

*Primary Examiner*—Alton D. Rollins
*Assistant Examiner*—Mark L. Berch
*Attorney, Agent, or Firm*—Bessie A. Lepper

[57] ABSTRACT

Novel 7-alkyl-(and 7-cycloalkyl-loweralkyl)9-hydroxy-4,4-di-lower-alkyl-1,2,3,4-tetrahydro-[1]benzopyrano[3,4-c]pyrroles; 7-alkyl-(and 7-cycloalkyl-lower-alkyl)9-hydroxy-4,4-di-lower alkyl-1,2,3,4,3a,9b-hexahydro[1]benzopyrano[3,4-c]pyrroles, and certain ester and ether derivatives thereof. These compounds exhibit CNS activity, and are useful as sedatives or tranquilizers.

2 Claims, No Drawings

BENZOPYRANS AND INTERMEDIATES FOR THE PREPARATION OF PYRROLO BENZOPYRANS

This application is a divisional application of Ser. No. 332,404, filed Feb. 14, 1973, now U.S. Pat. No. 3,888,946, which was a continuation-in-part of application Ser. No. 144,244 filed Mar. 17, 1971, now abandoned, which in turn was a continuation-in-part of Ser. No. 842,690 filed July 17, 1969, and now abandoned.

This invention relates to novel chemical compositions of matter known in the art of chemistry as 1,2,3,4-tetrahydro[1]benzopyrano[3,4-c]pyrroles, 1,2,3,4,3a,9b-hexahydro[1]benzopyrano [3,4-c]pyrroles, the intermediates therefor and to the preparation of the same.

The invention sought to be patented, in its composition aspct, resides in the concept of a class of chemical compounds which is designated as 7-alkyl-(and 7-cycloalkyl-lower-alkyl)9-hydroxy-4,4-di-lower-alkyl-1,2,3,4-tetrahydro[1]benzopyrano[3,4-c] pyrroles, 7-alkyl-(and 7-cycloalkyl-lower-alkyl)9-hydroxy-4,4-di-lower-alkyl-1,2,3,4,3a,9b-hexahydro[1]benzopyrano[3,4-c]pyrroles and certain ester and ether derivatives thereof. The tangible embodiments of this composition aspect of the invention possess the inherent use characteristics of having biological activity as determined by standard pharmacological test procedures for potential therapeutic drugs.

It is therefore a primary object of this invention to provide novel chemical compositions of matter, novel intermediates for synthesizing them and methods of forming the the chemical compositions and their intermediates. It is another object to provide chemical compositions which exhibit CNS and cardiovascular properties. Other objects of the invention will in part be obvious and will in part be apparent hereinafter.

The invention accordingly comprises the several steps and the relation of one or more of such steps with respect to each of the others, and the composition of matter possessing the characteristics, properties and the relation of components which wll be exemplified in the compositions hereinafter described and the scope of the invention will be indicated in the claims.

without limiting the generality of the foregoing, illustrative and preferred embodiments of our 7-alkyl-(and 7-cycloalkyl-lower-alkyl)9-hydroxy-4,4-di-lower-alkyl-1,2,3,4-tetrahydro[1]benzopyrano[3,4-c]pyrroles and 7-alkyl-(and 7-cycloalkyl-lower-alkyl)9-hydroxy-4,4-di-lower-alkyl-1,2,3,4, 3a,9b-hexahydro[1]benzopyrano[3,4-c]pyrroles are those of formulas I and II, respectively:

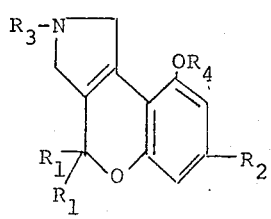

I

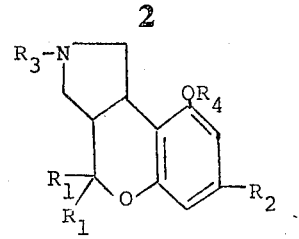

II wherein $R_1$ is lower-alkyl; $R_2$ is alkyl or cycloalkyl-lower-akyl; $R_3$ is hydrogen, lower-alkanoyl, cycloalkyl-lower-alkyl, cycloalkyl-lower-alkanoyl, lower-alkenyl, lower-alkynyl, halo-lower-alkenyl (including fluoro, chloro-, bromo-, and iodo-lower-alkenyl), phenyl-lower-alkyl, phenyl-lower-alkenyl, phenyl-lower-alkanoyl or phenyl-lower-alkynyl; and $R_4$ is hydrogen, lower-alkyl, lower-alkanoyl, carbamyl, N-lower-alkylcarbamyl, N,N-di-lower-alkyl-carbamyl, phosphonyl, dialkylaminoalkyl or an acid addition salt thereof, or dialkylaminoalkanoyl or acid addition salt thereof.

As used herein, the term "lower-alkyl" means saturated, monovalent aliphatic-radicals, including straight and branched-chain radicals of from one to six carbon atoms, as illustrated by, but not limited to methyl, ethyl, propyl, isopropyl, butyl, sec.-butyl, amyl, hexyl, and the like.

As used herein, the term "alkyl" means saturated, monovalent aliphatic radicals, including straight and branched-chain radicals of from one to twenty carbon atoms, as illustrated by, but not limited to methyl, n-amyl, n-hexyl, 2-heptyl, n-heptyl, 3-methyl-2-octyl, n-octyl, 2-nonyl, 2-tetradecyl, n-hexadecyl, 2-eicosanyl, and the like.

As used herein, the term "lower-alkenyl" means monovalent, aliphatic-radicals of from three to seven carbon atoms which contain at least one double bond, and are either straight or branched-chain, as illustrated by, but not limited to 1-(2-propenyl), 1-(3-methyl-2-propenyl), 1-(1,3-dimethyl-2-propenyl), 1-(2-hexenyl), and the like.

As used herein, the term "lower-alkynyl" means monovalent, aliphatic-radicals, of from three to seven carbon atoms which contain at least one triple bond, and are either straight or branched, as illustrated by, but not limited to 1-(2propynyl), 1-(1-methyl-2-propynyl), 1-(2-heptynyl), and the like.

As used herein, the term "cycloalkyl" means cyclic, saturated aliphatic-radicals of from three to eight carbon atoms, as illustrated by, but not limited to cyclopropyl, cyclobutyl, 2-methylcyclobutyl, cyclohexyl, 4-methylcyclohexyl, cyclo-octyl, and the like.

As used herein, the term "lower-alkanoyl" means saturated, monovalent, aliphatic radicals, derived from a monocarboxylic acid, including straight or branched-chain radicals of from one to six carbon atoms, as illustrated by, but not limited to formyl, acetyl, propionyl, α-methylpropionyl, butyryl, hexanoyl, and the like.

As used herein, the terms "phenyl-lower-alkyl", "phenyl-lower-alkenyl", "phenyl-lower-alkanoyl" and "phenyl-lower-alkynyl" means a monovalent radical consisting of a phenyl nucleus bonded to the rest of the molecule, respectively, through a divalent lower-alkylene radical of from one to four carbon atoms as illustrated by, but not limited to methylene, 1,1-ethylene, 1,2-ethylene, 1,3-propylene, 1,2-propylene, 1,4-butylene, and the like, or through a divalent lower-alkenylene radical of from two to four carbon atoms, as illustrated by, but not limited to 1,2-ethenylene, 1,3-(1-propenylene), 1,3-(1-butenylene), 1,4-(2-butenylene), and the like, or through a divalent lower-alkynylene radical of from two to four carbon atoms, as illustrated by, but not limited to 1,2-ethynylene, 1,3-propynylene, 1,3-(1-butynylene), and the like. Here and elsewhere throughout this specification, it will be understood the benzene ring of phenyl can bear any number and kind of substituents such as would occur to the man skilled in organic chemistry. Solely for illustration, and without limitation, such substituents include lower-alkyl, lower-alkoxy, halo (chloro, bromo, oido, or fluoro), nitro, lower-alkylmercapto, and the like.

Representative compounds of the present inventon include: 4,4-Dimethyl-9-hydroxy-7-(3-methyl-2-octyl)-1,2,3,4-tetrahydro[1]benzopyrano[3,4-c]pyrrole;
  9-Hydroxy-7-(3-methyl-2-octyl)-2,4,4-trimethyl-1,2,3,4-tetrahydro[1]benzopyrano[3,4-c]pyrrole;
  9-Acetoxy-4,4-diethyl-7-n-pentyl-1,2,3,4-tetrahydro[1]benzopyrano[3,4-c]pyrrole;
  4,4-Dimethyl-2-propargyl-7-(3-methyl-2-octyl)-tetrahydro[1]benzopyrano[3,4-c]pyrrole; and the like.

The compunds are central nervous system depressants and are useful as sedatives when administered to mammals in dosages of from 1 to 10 mg./kg. of body weight daily. The compounds are preferrably administered in divided doses, i.e., 0.25 to 2.5 mg./kg. of body weight four times daily. However, when employed as "night-time" sedatives, single doses at bedtime are used.

The invention, in one of its process aspects, is described as residing in the process of catalytically debenzylating, with hydrogen in the presence of a catalyst, the compounds of formula I hereinabove where $R$ is benzyl to produce the compounds of formula I where $R_3$ is hydrogen. The reaction is preferably carried out in an organic solvent inert under the conditions of the reaction, for example methanol, ethanol, isopropanol, and the like. Suitable catalysts are platinum or palladium-on-charcoal. A preferred catalyst is palladium-on-charcoal.

The invention, in another of its process aspects, is described as residing in the process of reacting the compounds of formulas I or II, where $R_3$ is hydrogen, with a cycloalkly-lower-alkyl halide, lower-alkenyl halide, lower-alkynyl halide, halo-lower-alkenyl halide, phenyl-lower-alkyl halide, phenyl-lower-alkenyl halide, or phenyl-lower-alkynyl halide to prepare the compounds of formulas I or II where $R_3$ is, respectively, cycloalkyl-lower-alkyl, lower-alkenyl, lower-alkynyl, halo-lower-alkenyl, phenyl-lower-alkyl, phenyl-lower-alkenyl, phenyl-lower-alkanoyl or phenyl-lower-alkynyl. The reaction is preferably carried out in an organic solvent inert under the conditions of the reaction, for example methanol, ethanol, isopropanol, or dimethylformamide, and in the presence of an acid-acceptor. The purpose of the acid-acceptor is to take up the hydrogen halide split out during the course of the reaction and is a basic substance which forms water-soluble salts readily separable from the reaction mixture. Suitable acid-acceptors are alkali metal carbonates or bicarbonates, for example sodium, or potassium carbonate, or bicarbonate, or alkali metal hydroxides, for example sodium or potassium hydroxide. The reaction can also be carried out in the presence of a molar excess of the base of formulas I or II where $R_3$ is hydrogen. A preferred acid-acceptor is sodium carbonate, and a preferred solvent is ethanol.

The invention, in still another process aspect, is described as residing in the process of reacting the compounds of formulas I or II, where $R_3$ is hydrogen, with an acid halide or anhydride of a lower-alkanoic, cycloalkyl-lower-alkanoic, or phenyl-lower-alkanoic acid to produce the compounds of formulas I and II where $R_3$ is, respectively, lower-alkanoyl, cycloalkyl-lower-alkanoyl, or phenyl-lower-alkanoyl. The reaction is preferably carried out in an organic solvent inert under the conditions of the reaction, for example benzene, toluene, xylene, and the like, and in the presence of a basic catalyst, for example pyridine, triethylamine, dimethylaniline, and the like. a preferred solvent is benzene, and a preferred basic catalyst is pyridine.

The invention, in still another process aspect, is described as residing in the process of reducing, with an alkali metal aluminum hydride, the compounds of formulas I or II were $R_a$ is cycloalkyl-lower-alkanoyl or phenyl-lower-alkanoyl and $R_4$ is hydrogen or lower-alkyl to produce the compounds of formula I where $R_3$ is, respectively, cycloalkyl-lower-alkyl or phenyl-lower-alkyl. The reaction is preferably carried out in an organic solvent inert under the conditions of the reaction, for example diethyl ether, tetrahydrofuran, dibutyl ether, and the like.

The invention, in still another of its process aspects, is described as residing in the process of reducing with hydrogen over a suitable catalyst the 7-alkyl-(and 7-cycloalkyl-lower-alkyl)9-hydroxy-4,4-di-lower-alkyl-1,2,3,4-tetrahydro[1]benzopyrano[3,4-c]pyrroles of formula I where $R_1$, $R_2$ and $R_4$ have the meanings given above and $R_3$ is hydrogen, lower alkanoyl, cycloalkyl-lower-alkyl, cycloalkyl-lower-alkanoyl, or phenyl-lower-alkyl or phenyl-lower-alkanoyl to produce the 7-alkyl-(and 7-cycloalkyl-lower-alkyl)9-hydroxy-4,4-di-lower-alkyl-1,2,3,4,3a,9b-hexahydro[1]benzopyrano[3,4-c]pyrroles of formula II where $R_3$ is hydrogen and $R_1$, $R_2$ and $R_4$ have the meanings given above. The reaction is carried out in a suitable liquid medium and under more drastic conditions, e.g., an acid medium such as acetic acid, hydrogen pressures over 50 psia. and stronger catalysts than used for debenzylating. Suitable catalysts include palladium-on-charcoal, platinum, Raney nickel, and the like. A preferred catalyst is 10% palladium on charcoal.

The ester and ether derivatives of the compounds of formulas I and II e.g., the compounds where $R_4$ is lower-alkyl, lower-alkanoyl, carbamyl, N-lower-alkylcarbamyl, N,N-di-lower alkyl-carbamyl, phosphonyl or a water-solubilizing substituent are prepared by reacting the corresponding compound where $R_4$ is hydrogen, preferably in the presence of a basic catalyst, with a lower-alkyl halide, to produce the compounds where $R_4$ is lower-alkyl; with a lower-alkanoic anhydride (or mixed anhydride), to produce the compounds where $R_4$ is lower-alkanoyl; with a molar equivalent of phosgene followed by reaction of the resulting chloroformate with ammonia, a lower-alkylamine, or a di-lower-alkylamine, to produce the compounds where $R_4$ is, respectively, carbamyl, N-lower-alkylcarbamyl, or N,N-di-lower-alkylcarbamyl; or with one molar equivalent amount of phosphorus oxychloride followed by reaction of the resulting dichlorophosphinate with aqueous sodium or potassium carbonate, to produce the compounds where $R_4$ is phosphonyl. Suitable solvents are benzene, toluene, xylene and the like, and suitable basic catalysts are alkali metal carbonates, bicarbonates, or hydroxides, dimethylaniline, pyridine, and the like.

Where $R_4$ is dialkylaminoalkyl, of the structure $-C(CH_2)_xNR_5R_6$ wherein x is 1 through 6 and $R_5$ and $R_6$ are lower-alkyl, the compounds may be formed by reacting the appropriate pyrano benzopyran with an alkali alkoxide in a solvent, such as ethanol, to give the alkali derivative, which upon treatment with a dialkylaminoalkyl halide in a solvent, such as benzene, results in the formation of the desired derivatives. The acid addition salts of the dialkylaminoalkyl derivatives may be prepared by reacting the free base with an appropriate acid in a suitable organic solvent, in which case the acid salts may be separated directly or obtained by concentration of the solvent.

Where $R_4$ is dialkylaminoalkanoyl, of the structure $-CO(CH_2)_xNR_5R_6$ wherein x is 1 through 6 and $R_5$ and $R_6$ are lower alkyl, the appropriate pyrano benzopyran is reacted with equimolar amounts of carbodiimide and the appropriate acid or acid salt of the amino group to give either the free base or the acid addition salt directly. If the free base form is obtained, then it may be converted to the acid addition salt in the same manner as described for preparing the acid addition salt of the dialkylaminoalkyl derivative. It is well known that it is possible to convert from one acid addition salt to another by regenerating the free base form and acidifying it.

The compounds of formula I where $R_3$ is benzyl, and which, as described hereinabove, are used as intermediates for the preparation of the compounds of formulas I and II where $R_3$ has the other various meanings given hereinabove, are in turn prepared by reacting a 7-alkyl-(or 7-cycloalkyl-lower-alkyl.) 9-hydroxy-4-oxo-1,2,3,4-tetrahydro[1]benzopyrano[3,4-c]pyrrole having the formula III

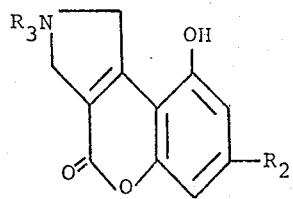

with a lower-alkyl magnesium halide as illustrated by the equation

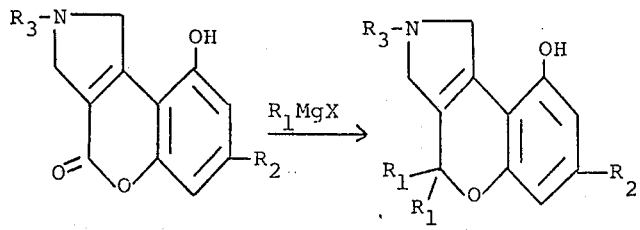

where $R_1$, $R_2$, and $R_3$ have the meanings given hereinabove, and x represents a halogen. The reaction is carried out in an organic solvent inert under the conditions of the reaction. Suitable solvents are diethyl ether, dibutyl ether, tetrahydrofuran, anisole, pyridine, and the like. It is preferred to add a solution of the 7-alkyl-(or 7-cycloalkyl-lower-alkyl)-9-hydroxy-4-oxo-1,2,3,4-tetrahydro[1]benzopyrano[3,4-c]pyrrole in a pyridine or anisole solution, or in a mixture of these solvents, to a solution of the Grignard reagent in anisole.

The compounds of formula III where $R_3$ is benzyl in turn are prepared by reacting an ethyl-1-benzyl-4-pyrrolidone-3-carboxylate of formula V with a 5-alkylresorcinol (or a 5-cycloalkyl-lower-alkylresorcinol of formula VI. The reaction is carried out in a mixture of concentrated sulfuric acid and phosphorus oxychloride or in the presence of other condensation agents such as aluminum chloride, hydrogen chloride, or polyphosphoric acid and is illustrated by the equation:

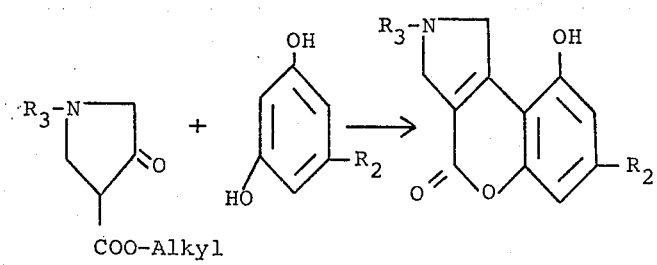

where $R_2$ is defined as above and $R_3$ is benzyl.

The intermediate 5-alkyl- or 5-cycloalkyl-loweralkyl-resorcinols of formula VI are conveniently prepared by methods generally known in the art comprising dehydration of a 3,5-di-lower-alkoxyphenyl alkyl (or cycloalkyl-lower-alkyl) carbinol, reduction of the resulting 3,5-di-lower-alkoxyphenylalkene (or di-lower-alkoxyphenyl-cycloalkyl-lower-alkene), and hydriodic acid cleavage of the ether groups to the corresponding 5-alkyl- (or 5-cycloalkyl-lower-alkyl-) resorcinol. The starting carbinols in turn are prepared by reaction of an appropriate Grignard reagent with a 3,5-di-lower-alkoxybenzoic acid ester, amide, or 3′,5′-di-lower-alkoxy-alkanophenone (or 3′,5′-di-lower-alkoxy-cycloalkyl-lower alkanophenone).

The intermediate pyrrolidone carboxylates of formula V may be prepared by the method of Jaeger and Beal, J. Org. Chem. 30, 742 (1965).

Due to the presence of a basic tertiary amino grouping, the compounds of this invention form acid-addition and quaternary ammonium salts. The compounds of formulas I and II, in free base form, are converted to the acid-addition salt form by interaction of the base with an acid. In like manner, the free bases can be regenerated from the acid-addition salt form in the conventional manner, that is by treating the salts with strong aqueous bases, for example alkali metal hydroxides, alkali metal carbonates, and alkali metal bicarbonates. The bases thus regenerated can then be interacted with the same or a different acid to give back the same or different acid-addition salt. Thus the novel bases and all of their acid-addition salts are readily interconvertible.

The quaternary ammonium salts of the compounds of formulas I and II are obtained by the addition of esters of strong acids to the free base form of the compounds, said esters having a molecular weight less than about 300. A preferred class of esters comprises alkyl, alkenyl, and phenyl-lower-alkyl esters of strong inorganic acids or organic sulfonic acids, including such compounds as methyl chloride, methyl bromide, methyl iodide, ethyl bromide, propyl chloride, allyl chloride, allyl bromide, methyl sulfate, methyl benzenesulfonate, methyl p-toluenesulfonate, benzyl chloride, benzyl bromide, and substituted benzyl halides, for example p-chlorobenzyl chloride, 3,4-dichlorobenzyl chloride, pentachlorobenzyl chloride, p-nitrobenzyl chloride, p-methoxybenzyl chloride, and the like.

It will thus be appreciated that each of formulas I and II not only represents the structural configuration of the bases of our invention but each is also representative of the respective structural entity which is common to all of our respective compounds of formulas I and II whether in the form of the free bases or in the form of the salts of the bases. We have found that by virtue of this common structural entity, the bases and their acid-addition salts as well as the quaternary ammonium salts have inherent pharmacodynamic activity of a type to be more fully described hereinbelow. This inherent pharmacodynamic activity can be enjoyed in useful form for pharmaceutical purposes by employing the free bases themselves or the acid-addition salts formed from pharmaceutically-acceptable acids or esters of strong acids, that is, acids or esters of strong acids, that is, acids or esters whose anions are innocuous to the animal organism in effective doses of the salts so that beneficial properties inherent in the common structural entity represented by the free bases are not vitiated by side-effects ascribable to the anions.

In utilizing this pharmacodynamic activity of the salts of the invention, we prefer of course to use pharmaceutically-acceptable salts. Although water-insolubility, high toxicity, or lack of crystalline character may make some particular salt species unsuitable or less desirable for use as such in a given pharmaceutical application, the water-insoluble or toxic salts can be converted to the corresponding pharmaceutically-acceptable bases by decomposition of the acid-addition salt with aqueous base as explained above, or alternatively, the acid-addition salt can be converted to any desired pharmaceutically-acceptable acid-addition salt by double decomposition reactions involving the anion, for example, by ion-exchange procedures.

As in the base of the acid-addition salts, water-insolubility, high toxicity, or lack of crystalline character may make some quaternary ammonium salt species unsuitable or less desirable for use as such in a given pharmaceutical application. The water-insoluble or toxic salts can be converted to the corresponding pharmaceutically-acceptable salts by double decomposition reactions involving the anion, for example, by ion-exchange procedures. Alternatively, if the anion of the original quaternary salt forms a water-insoluble silver salt, the quaternary salt will react with silver oxide in aqueous medium to form the corresponding quaternary ammonium hydroxide, the original anion being removed as a precipitate. The quaternary ammonium hydroxide solution can then be neutralized with any desired acid, weak or strong, to produce a new quaternary ammonium salt in which the anion is different from that of the original salt. In this way quaternary ammonium salts in which the anion is derived from a weak acid are formed.

Moreover, apart from their usefulness in pharmaceutical applications, our salts are useful as characterizing or identifying derivatives of the free bases or in isolation or purification procedures. Such characterizing or purification acid addition salt derivatives, like all of the acid-addition salts, can, if desired, be used to regenerate the pharmaceutically-acceptable free bases by reaction of the salts with aqueous base, or alternatively the acid-addition or quaternary ammonium salt can be converted to a pharmaceutically-acceptable salt by, for example, ion-exchange procedures.

It will be appreciated from the foregoing that all of the acid-addition and quaternary ammonium salts of our new bases are useful and valuable compounds regardless of considerations of solubility, toxicity, physical form, and the like and accordingly are within the purview of the instant invention.

The novel features of the compounds of the invention, then, reside in the concept of the bases and the cationic forms of the new compounds of formulas I and II and not in any particular acid or ester moiety or anion associated with the salt forms of the compounds; rather, the acid or ester moieties or anions which can be associated in the salt forms are in themselves neither novel nor critical and therefore can be any anion or acid-like substance capable of salt formation with bases. In fact, in aqueous solutions, the base form or watersoluble acid-addition salt form of the compounds of the invention both possess a common protonated cation or ammonium ion.

Thus appropriate acid-addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylene dicarboxylic acid, sorbic acid, 2-furancarboxylic acid, cholic acid, pyr-necarboxylic acid, 2-pyridinecarboxylic acid, 3-indoleacetic acid, quinic acid, sulfamic acid, methane-sulfonic acid, isethionic acid, benzene-sulfonic acid, p-toluene-sulfonic acid, benzenesulfinic acid, butylarsonic acid, diethylphosphinic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pryophosphoric acid, arsenic acid, picric acid, picrolonic acid, barbituric acid, boron trifluoride, and the like.

The acid-addition salts are prepared either by dissolving the free base in an aqueous solution containing the appropriate acid and isolating the salt by evaporating the solution, or by reacting the free base and acid in an organic solvent, in which case the salt separates directly or can be obtained by concentration of the solution.

The quaternary ammonium salts are prepared by mixing the free base and an appropriate alkyl halide in an inert solvent. Heating may be used to facilitate the reaction, although salt formation usually takes place readily at room temperature. The quaternary ammonium salt separates directly or can be obtained by concentration of the solution.

The compounds of formulas I and II have been shown to possess central nervous system depressant activity as evidenced by gross overt changes induced by intravenous administration in mice in standard tests involving observations of psychomotor activity, reactivity to stimuli, and ability to perform normal, non-conditioned motor tasks. This activity indicates their usefulness as psychotropic agents. In addition, some of these compounds exhibit hypotensive effects on the cardiovascular system which indicates their usefulness as antihypertensive agents.

The compounds can be prepared for use by dissolving under sterile conditions a salt form of the compounds in water (or an equivalent amount of a nontoxic acid if the free base is used) or in a physiologically compatible aqueous medium such as saline, and stored in ampoules for intramuscular injection. Alternatively, they can be incorporated in unit dosage form as tablets or capsules for oral administration either alone or in combination with suitable adjuvants such as calcium carbonate, starch, lactose, talc, magnesium stearate, gum acacia, and the like. Still further the compounds can be formulated for oral administration in aqueous alcohol, glycol or oil solutions or oil-water emulsions in the same manner as conventional medicinal substances are prepared.

The molecular structures of the compounds of our invention were assigned on the basis of study of their infrared, ultraviolet and NMR spectra and their transformation products, and confirmed by the correspondence of calculated and found values for the elementary analyses for representative examples.

The following examples will further illustrate the invention without, however, limiting it thereto.

EXAMPLE 1

4,4-Dimethyl-9-hydroxy-7-(3-methyl-2-octyl)-1,2,3,4-tetrahydro[1]benzopyrano[3,4-c]pyrrole A.
2-Benzyl-4-oxo-9-hydroxy-7-(3-methyl-2-octyl)-1,2,3,4tetrahydro[1]benzopyrano[3,4-c]pyrrole This first intermediate was prepared by the following reaction:

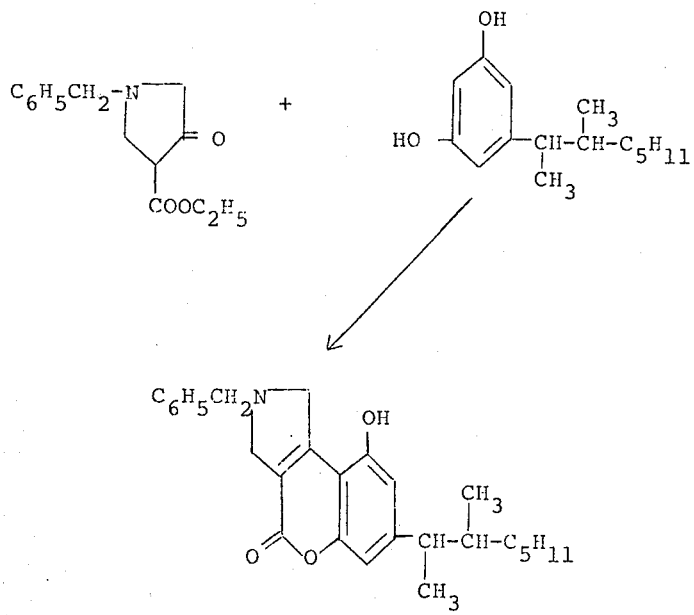

The ethyl 1-benzyl-4-pyrrolidone-3-carboxylate was prepared in 40% yield (5 g) from 14.7 g of diethyl 13.benzyl.3.azaadipate and 5.6 g of potassium t-butoxide according to the procedure of E. Jaeger and J. H. Beal, J. Org. Chem. 30, 742 (1965). It was a colorless, slightly cloudy oil with $n_D^{25}$ 1.5147 (lit. $n_D^{25}$ 1.5264). The infrared spectrum was the same as the published value.

The 5-(3-methyl-2-octyl) resorcinol was prepared by the method of Adams, MacKenzie and Loewe, JACS 70, 664-8 (1948).

In each of three flasks a stirred and cooled mixture of 10 g (0.04 mole) of ethyl 1-benzyl-4-pyrrolidone-3-carboxylate and 10 g (0.04 mole) of 5-(3-methyl-2-octyl) resorcinol was dissolved by addition of 25 ml of concentrated sulfuric acid, and then 15 ml of phosphorus oxychloride was added to each flask. The mixtures were stirred at room temperature for 4 days, with a subsequent addition of 6 ml of phosphorus oxychloride to each. Then they were poured over ice with stirring. The resulting granular yellow solid was filtered and taken up in chloroform. The solution was washed repeatedly with 10% sodium bicarbonate solution and then with water. Evaporation of the dried ($Na_2SO_4$) extract yielded 30 g of a clear yellow gum. A portion of the gum was converted to the hydrochloride, which, after several recrystallizations from acetonitrile/ether, melted at 190°–193°. Infrared and ultraviolet spectra were in good agreement with the assigned structure. The substance exhibited $\lambda_{max}^{EtOH}$ 316 m$\mu$ (log $\epsilon$ 4.098).

Anal. Calcd. for $C_{27}H_{34}ClNO_3$: C, 71.27; H, 7.31; N, 3.08. Found: C, 71.27; H, 7.49; N, 3.02.

Alternatively, the crude pyrone gum may be used directly in the Grignard reaction.

B.
2-Benzyl-4,4-dimethyl-9-hydroxy-7-(3-methyl-2-octyl)-1,2,3,4-tetrahydro[1]benzopyrano[3,4-c]pyrrole This second intermediate was prepared by the following reaction:

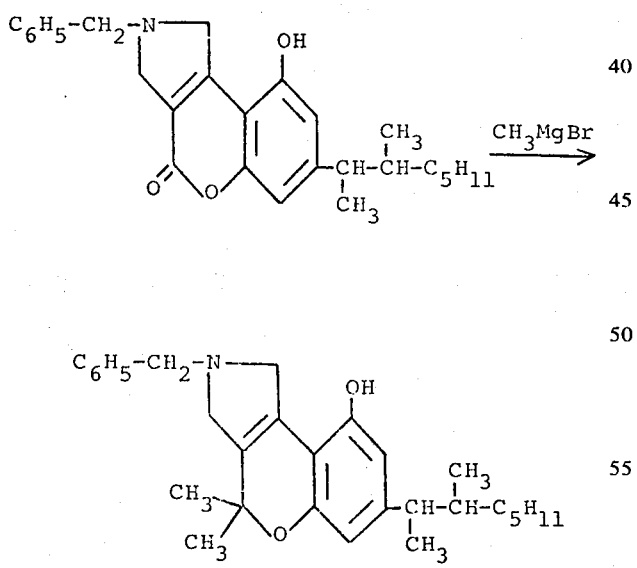

The pyrone, both as the crude yellow gum (above and as the free base obtained from the hydrochloride, gave the pyran upon reaction with the methyl Gignard reagent. The crude gum actually was preferred, because with it the overall yield from ethyl 1-benzyl-4-pyrrolidone-3-carboxylate was 24% (22.7 g of the gum yielded 9.7 g of pyran), whereas the overall yield in the two steps through the hydrochloride was not more than half as great. A typical reaction was carried out as follows.

A solution of 4.2 g (0.01 mole) of the pyrone (prepared from its hydrochloride) in 50 ml of dry anisole was added dropwise under nitrogen to a stirred suspension of 12 g (0.1 mole) of methylmagnesium bromide in anisole. The reaction mixture was stirred at 60° for 3 days, then was decomposed with 50 ml of water and 50 ml of 4N sulfuric acid. Removal of the anisole by steam distillation left the product as a brown gum insoluble in water. A solution of the gum in chloroform was washed with 10% sodium bicarbonate and with water, and was dried over sodium sulfate. Evaporation yielded a dark gum, which upon trituration with acetonitrile gave 2.4 g (56%) of the pyran as a colorless solid, m.p. 175°–180°. It exhibited $\lambda_{max}^{EtOH}$ 290 m$\mu$ (log $\epsilon$ 4.049). N.M.R. and infrared spectra were in good agreement with the proposed structure.

The 2-benzyl-4-dimethyl-9-hydroxy-7-(3-methyl-2-octyl)-1,2,3,4-tetrahydro[1]benzopyrano[3,4-c]pyrrole was evaluated pharmocologically by the oral route as a tranquilizer in mice. It was found to reduce mouse fighting by 60% at 10mg/kg doses. This compound also reduced blood pressure in spontaneously hypertensive rats at 10mg/kg.

The final pyrrole was prepared by reduction of the pyran according to the following reaction:

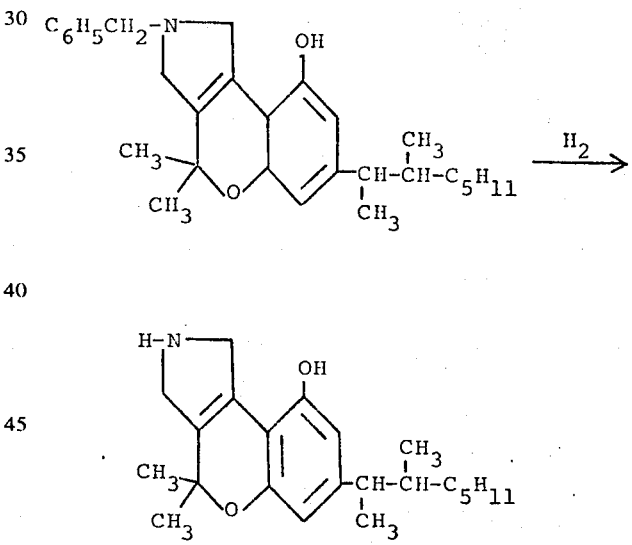

14.1 grams of the pyran thus prepared, as the hydrochloride salt, was hydrogenated in 250 milliliters of 95% ethanol in the presence of 1 gram of 5% palladium on charcoal for 3 hours. The hydrogenation was conducted at a pressure of 3 atmospheres. The reaction was filtered, the ethanol was removed, carbon tetrachloride was added and the $CCl_4$ solvent was then stripped off. Chloroform, sodium bicarbonate and water were added and the reaction mixture was stirred for 1 hour. It was then dried over magnesium sulfate and concentrated to approximately 150 milliliters, whereupon 2 grams of solid product, melting point 201°–204° C, crystallized out. The solution was further concentrated and hot acetonitrile was added to obtain some additional solid product.

Nuclear Magnetic Resonance (NMR) spectra were used to identify the product as the desired compound.

Anal. Calcd. for $C_{22}H_{33}NO_2$: C, 76.92; H, 9.68; N, 4.08. Found: C, 76.62; H, 9.83; N, 3.98.

The 4,4-dimethyl-9-hydroxy-7-(3-methyl-2-octyl)-1,2,3,-4-tetrahydro[1]benzopyrano[3,4-c]pyrrole produced was evaluated for its pharmacological properties. It was found that when given orally to mice that it showed marked (3) activity as an antidepressant for 4 hours at dosages of 10 and 20mg/kg in the modified dopa test as described by Everett, Fed. Proc. 23 p. 198 (1964). In oral dosages of 10mg/kg it reduced fighting 40% in the mouse fighting test, indicating it to be a mild tranquilizer.

The 2-benzyl-4,4-dimethyl-9-hydroxy-7-(3-methyl-2-octyl)-1,2,3,4-tetrahydro[1]benzopyrano[3,4-c]pyrrole may be reacted with potassium ethoxide to give the potassium derivative of phenol which on treatment with dimethylaminoethyl chloride in a suitable solvent, such as benzene, will give the corresponding compound where $R_4$ is dimethylaminoethyl.

EXAMPLE 2

4,4-Dimethyl-9-hydroxy-7-(3-methyl-2-octyl)-2-propargyl-1,2,3,4-tetrahydro[1]benzopyrano[3,4-c]pyrrole 1.23 grams of the 4,4-dimethyl-9-hydroxy-7-(3-methyl-2-octyl)-1,2,3,4-tetrahydro[1]benzopyrano[3,4-c]pyrrole was dissolved in 5 milliliters of hexamethyl phosphoric triamide. While the solution was cooling, 0.24 grams of propargyl bromide, dissolved in 1.5 milliliters of hexamethyl phosphoric triamide was added. The reaction was stirred for 16 hours, and 20 milliliters of water was added thereto, whereupon crystals formed. The crystals were removed by filtration, washed with water and recrystallized from a mixture of ether and a hydrocarbon boiling at 63°–70° C to yield 0.44 gram of a compound having a melting point of 150°–152° C. The filtrate was neutralized with potassium carbonate and 0.444 gram of the compound identified to have the structure

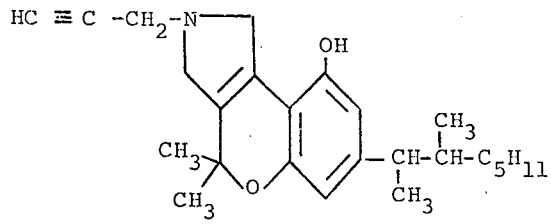

was obtained.

This propargyl derivative exhibited moderate (2) activity as an anti-depressant at 20mg/kg dosages as measured by the modified dopa test. Oral dosages of 10mg/kg reduced figing 36% in the mouse fighting test illustrating its use as a tranquilizer.

EXAMPLE 3

4,4-Dimethyl-9-hydroxy-7-(3-methyl-2octyl)-1,2,3,4-3a,9b-hexahydro[1]benzopyrano[3,4-c]pyrrole A solution of 2 g (0.0045 mole) of the pyran of Example 1B in 200 ml of absolute alcohol and 5 ml of glacial acetic acid was shaken under hydrogen at 55 psi with 0.5 g of 10% palladium-on charcoal. Hydrogenolysis was complete after 3 hours. The mixture was filtered and evaporated, and the residue was dissolved in chloroform. The chloroform solution was shaken to neutrality with 10% sodium bicarbonate solution, washed with water, dried over sodium sulfate, and evaporated. Upon trituration with acetonitrile, the gummy residue gave 1.25 g (79%) of a hygroscropic material, m.p. 128°–130°. Recrystallization from acetone gave an analytical sample, m.p. 131°–133°. N.M.R. and infrared spectra confirmed the assigned structure.

Anal. Calcd. for $C_{22}H_{36}NO_2$: C, 76.30; H, 10.40; N, 4.05. Found: C, 76.74; H, 9.80; N, 4.12.

It will thus be seen that the objects set forth above, among those made apparent from the preceding description, are efficiently attained, and, since certain changes may be made in carrying out the above method and in the composition set forth without departing from the scope of the invention, it is intended that all matter contained in the above description shall be interpreted as illustrative and not in a limiting sense.

We claim:

1. A compound of the formula

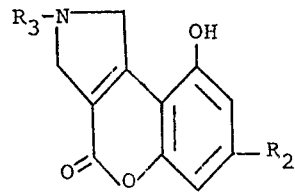

wherein $R_2$ is alkyl or cycloalkyl-lower-alkyl; and $R_3$ is hydrogen or benzyl; the lower alkyl groups having from 1 through 6 carbon atoms, the alkyl groups having from 1 through 20 carbon atoms and the cycloalkyl groups having from 3 to 8 ring carbon atoms.

2. A compound according to claim 1 wherein $R_2$ is 3-methyl-2-octyl and $R_3$ is benzyl and the compound is 2-benzyl-4-oxo-9-hydroxy-7-(3-methyl-2-octyl)-1,2,3,4-tetrahydro[1]benzopyrano[3,4-c]pyrrole.

* * * * *